(12) United States Patent
Crowe (10) Patent No.: US 9,352,061 B2
(45) Date of Patent: May 31, 2016

(54) SCENTED / LIGHTED/ AUDIO COMMUNICATION BALLOON AND VALVE

(76) Inventor: Jonathan M. Crowe, Kountze, TX (US)

( * ) Notice: Subject to any disclaimer, the term of this patent is extended or adjusted under 35 U.S.C. 154(b) by 431 days.

(21) Appl. No.: 11/390,745

(22) Filed: Mar. 28, 2006

(65) Prior Publication Data

US 2007/0235553 A1    Oct. 11, 2007

(51) Int. Cl.
| | | |
|---|---|---|
| A24F 25/00 | (2006.01) | |
| A61L 9/04 | (2006.01) | |
| B05B 15/00 | (2006.01) | |
| B05B 17/00 | (2006.01) | |
| A61L 9/12 | (2006.01) | |
| A63H 27/10 | (2006.01) | |

(52) U.S. Cl.
CPC ... *A61L 9/04* (2013.01); *A61L 9/12* (2013.01); *A63H 27/10* (2013.01); *A61L 2209/12* (2013.01); *A63H 2027/1058* (2013.01)

(58) Field of Classification Search
CPC ......... A61L 9/04; A61L 9/12; A61L 2209/12; A61L 9/048; A61L 9/01; A63H 27/10; A63H 2027/1058; A63H 2027/1083; A63F 2250/021; A01M 1/2055; A01M 2200/012
USPC ............... 239/60, 34, 289; 446/222; 251/144, 251/147; 137/223
See application file for complete search history.

(56) References Cited

U.S. PATENT DOCUMENTS

| | | | | |
|---|---|---|---|---|
| 2,783,084 A | * | 2/1957 | Paxton | 239/59 |
| 2,996,834 A | * | 8/1961 | Berlow | 446/220 |
| 3,080,138 A | * | 3/1963 | Church | 244/31 |
| 4,405,467 A | * | 9/1983 | Sato et al. | 252/1 |
| 4,438,588 A | * | 3/1984 | Martin | 446/222 |
| 4,452,393 A | * | 6/1984 | Schimanski et al. | 239/57 |
| 4,586,456 A | * | 5/1986 | Forward | 116/210 |
| 4,737,133 A | * | 4/1988 | Neumeier | 446/397 |
| 4,813,174 A | * | 3/1989 | Cook | 43/107 |
| 4,828,176 A | * | 5/1989 | Crowe | 239/60 |
| 5,115,976 A | * | 5/1992 | Weiss et al. | 239/57 |
| 5,335,689 A | * | 8/1994 | Reittu | 137/231 |
| 5,496,203 A | * | 3/1996 | Murray | 446/222 |
| 5,531,401 A | * | 7/1996 | Newcomb | 244/31 |
| 5,732,530 A | * | 3/1998 | Pfaff | 53/403 |
| 5,882,240 A | * | 3/1999 | Larsen | 446/225 |
| 6,146,001 A | * | 11/2000 | Cwiakala | 362/267 |
| 6,238,067 B1 | * | 5/2001 | Hirsch | 362/352 |
| 6,422,912 B1 | * | 7/2002 | Summers | 446/184 |
| 6,430,804 B1 | * | 8/2002 | Nelson et al. | 29/566 |
| 2002/0153687 A1 | * | 10/2002 | Howard | 280/90 |

* cited by examiner

*Primary Examiner* — Len Tran
*Assistant Examiner* — Steven M Cernoch
(74) *Attorney, Agent, or Firm* — Wilson Daniel Swayze, Jr.

(57) ABSTRACT

A balloon valve assembly for cooperating with a balloon includes a neck fitting to extend beyond a neck of the balloon, a collar portion to accept the balloon and the neck fitting. A change of pressure from the balloon urges the balloon and the collar portion together. The valve assembly is adapted to secure accessories that affect the five senses of sight, hearing, smell, taste and touch.

25 Claims, 5 Drawing Sheets

SCENTED / LIGHTED/ AUDIO COMMUNICATION BALLOON AND VALVE

FIELD OF THE INVENTION

The present invention relates generally to scented balloons, lighted or illuminated balloons, musical, or audio communication balloons and interlocking valve assemblies.

BACKGROUND OF THE INVENTION

No improved scented balloons, scented and light balloons, scented and musical balloons, lighted and musical balloons, lighted balloons, musical balloons, scented-lighted-musical balloons or devices adapted for the combination purposes of sealing balloons and permitting the emission of the mixed combinations of fragrances, lighting, and audio communication are known to applicant. Most balloon valves heretofore, whether of the two-piece variety or one-piece, have been of the type that are inserted into the neck of a balloon or the type that requires the neck of a balloon to be stretched over the outer body of the valve assembly. In the two-piece variety, sealing is completed by insertion of a plug valve having a bore formed there through into the neck of the balloon then inserting the final sealing piece into the bore with a light bulb on a tube inside the balloon but having electrical wires extending out the assembly to a power source. In the one-piece variety, the valve means is rigidly attached to the interior portion of the valve assembly, which is usually small enough to be swallowed by a child. Some assemblies use no valve at all but just seal the balloon neck with a tied ribbon and have lighted or musical devices attached to or freely dangle in the interior of the balloon body. In the two-piece or one-piece varieties, there exist disadvantages of being an attraction to unsupervised children whom can easily swallow small parts or subjected to free flowing devices that can be harmful to anyone.

The above noted balloon valve assemblies also have a tendency to separate from the balloon and pose danger for small children. In addition, neither variety has the means to safely encapsulate a fragrance, light, or tone-carrying medium.

U.S. Pat. No. 4,828,176 dated May 9, 1989 discloses a valve assembly for use with an inflatable article incorporated by reference in its entirety.

SUMMARY OF THE INVENTION

An objective of this invention is to provide a low cost and easily assembled combination of elements to cooperate with a balloon or other inflatable article for use in a wide variety of applicable settings.

A further object of the present invention is to provide a balloon neck fitting adapted to be fitted exterior to the balloon so as to permit the balloon neck to be pulled through and around a collar and to provide a mechanical interlocking fit between the collar, the interior heck portion of the balloon and the interlocking member of the plug valve.

Another object of the present invention is to provide a balloon valve assembly with a safety strap connecting the collar and the seal plug valve.

Another object of the present invention is to provide a balloon valve assembly which includes a collar portion and a sealing member of a plug valve where the sealing member is urged toward a more secure sealing position when the balloon is subjected to a sudden increase. In pressure, regardless of whether the sealing member was initially in interlocking engagement with said balloon and the collar portion or was initially only partially inserted into the collar portion.

Another object of the present invention is to provide an improved valve assembly to safely carry a fragrance emitting medium and to permit the diffusion of the fragrance from the fragrance emitting medium; still another object is to provide an apparatus for scenting the balloon bodies themselves.

More particularity, the improved valve assembly with the extended plug valve cup and/or collar ring portion protects the balloon neck from breaking during inflation by preventing an excessive concentration of volatile oil from being distributed at the balloon neck and body tangent.

Still another object is to provide the valve assembly to safely carry a valve—basket—insert that safely carries in the "basket" a light emitting diode (LED) and/or an electronic music—producing device of which have a button cell battery with integrated circuitry providing power to the assembly therein. Still another object is to provide an apparatus for any singular or combination of lighting or audio communication with scents emitting from within balloons in general.

Another object of the present invention is to provide secured exterior optional accessories to the valve assemblies optional bottom receiving cup. The "optional bottom receiving cup" is designed to securely receive accessories to include but not limited to a heat source for rapid evaporation of a stored scent of volatile oil in the tablets, a suction cup for attaching to any smooth surface, a mini digital recorder with rewinding time, a straw or stick for holding, a mini electronic music producing device, a gondola for total appearance of a miniature hot air balloon, a radio control gondola with fan receiver/propulsion system and hand held transmitter/controller, etc.

Another object of the present invention is to provide a modified plug valve flange with a one way check valve fill tube for introducing air or helium into the bottom of a pre-assembly through an unobstructed passageway for total inflation.

The present invention provides a child-proof safety valve and assembly for retention of fragrance tablet(s) and/or other compact devices and; thereon the outside bottom of the valve flange may be coated with a bitter tasting but harmless pure vegetable product proven effective in stopping thumb sucking and nail biting. The taste of this on the "valve flange" may be an unpleasant taste and aides in a deterrent for small children to place the device in their mouth.

Other features and advantages of present invention will be apparent from the following detailed description, the accompanying drawings and the appended claims.

DESCRIPTION OF THE PREFERRED EMBODIMENTS

Balloon valve assemblies according to preferred embodiments of the invention will now be described with reference to the drawings.

Figure 1:
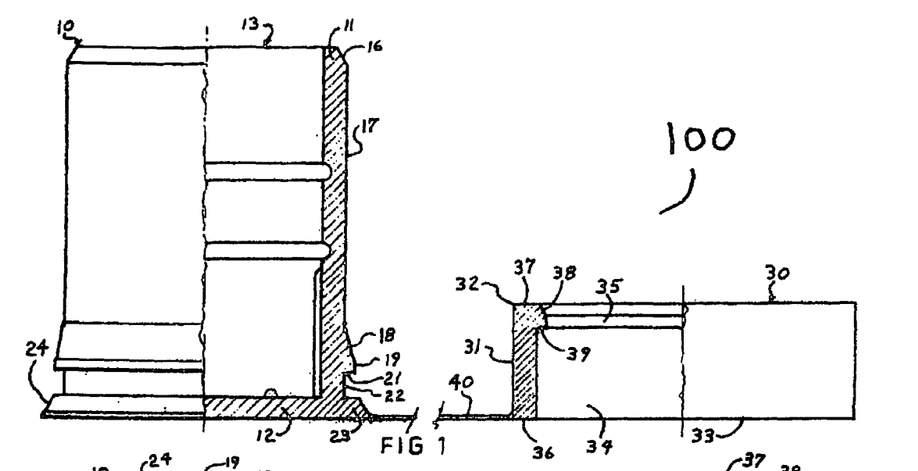
FIG. 1 is a side view of the preferred embodiment of the present invention.
Figures 2, 3, 4, 5, 6:
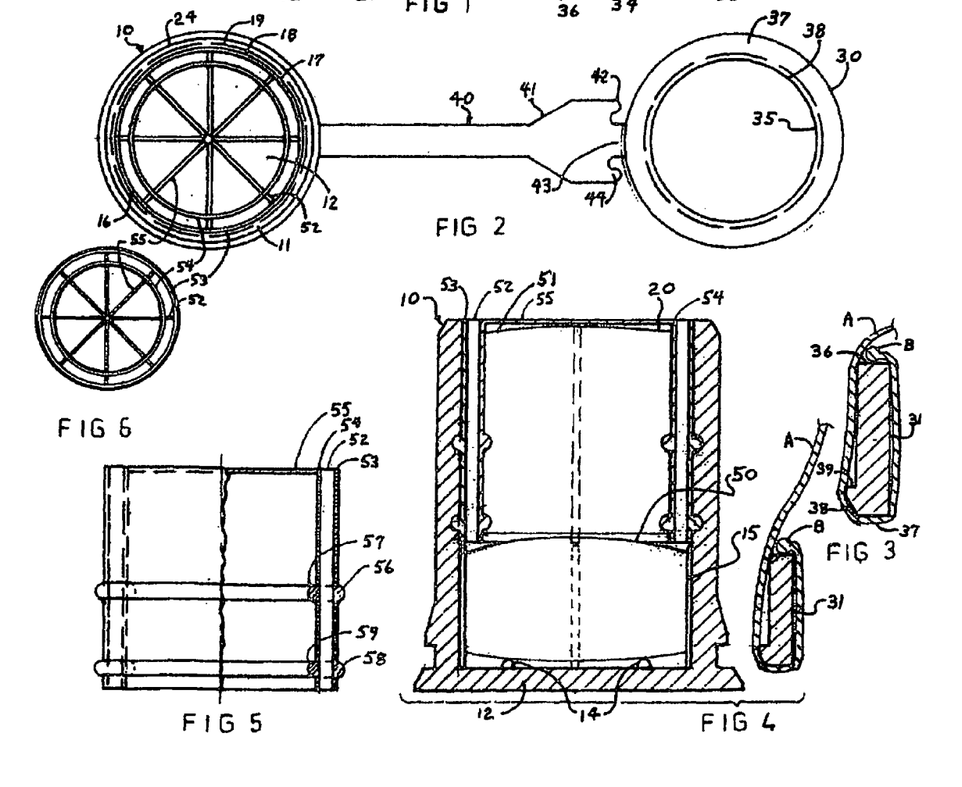
FIG. 2 is a top view of the embodiment shown in FIG. 1 and FIG. 4.
FIG. 3 is a sectional view of a portion of the collar ring portion with a balloon inserted.
FIG. 4 is a sectional view of the collar ring portion engaged with the plug valve neck assembly but spaced apart for clarity.
FIG. 5 is a side view of a valve—basket—insert with a sectional view.
FIG. 6 illustrates a plan view or top view of the FIG. 5 basket.

FIG. 1 illustrates a plug valve neck fitting 10, a collar ring portion 30, and a connecting member 40. As shown in FIG. 1, a balloon valve assembly 100 constructed according to a preferred embodiment of the present improvement invention including a neck fitting 10 which has a longitudinal length such that the neck fitting 10 extends beyond the balloon neck and which protects the balloon neck from breaking during inflation by preventing a sufficiently large concentration of the volatile oil from being distributed first at the balloon neck and balloon body tangent. The entire valve assembly may be made of plastic and is designed so as to permit the entire assembly to be cast or formed. The lateral wall 11 of neck fitting 10 has its outer end closed by an outer end cap or plug 12. The inner end 13 of neck fitting 10 is open to the gases interior to balloon A, and the interior of said neck fitting 10 is preferably sized so as to snugly accommodate by a friction fit one of a fragrance-carrying medium or "pill", a basket holding a light emitting diode (LED) and/or an audio producing device with power source therein. Fragrance-carrying media may be conveniently formed into small, cylindrical, solid tablets imbued with aromatic fragrances or scent as may be desired. Interior to the end cap 12, as shown in FIG. 4, are a number of raised platforms 14 spaced apart about the center of the interior portion of the end cap 12; these raised platforms 14 extend radially and serve to elevate the fragrance tablet from the interior side of the end cap 12 and thereby permit both ends of the fragrance table to be exposed to the gases of balloon A. As also shown in FIG. 4, a preferred embodiment includes a plurality of longitudinal ribs 15 spaced apart around the interior circumferential wall 20 of neck fitting 10. These longitudinal ribs 15, preferably slightly resilient, serve both to secure the fragrance tablet and to permit the cylindrical wall portion of the fragrance tablet to be exposed to the gases interior to the balloon A. In this manner, substantially the entire surface of the fragrance tablet is exposed to the interior gases while, simultaneously and advantageously, the tablet is held securely in place, avoiding concentrating the fragrance oil at any particular surface of the balloon. With a fragrance tablet sized smaller in diameter than an imaginary circle circumscribing the vertical ribs 15, it is found that the fragrance tablet is secured not only frictionally but with a mechanical inter-fit as well inasmuch as the vertical ribs 15, being preferably only slightly resilient, may cause a slight mechanical deformation of the side walls of the fragrance tablet upon insertion. The result is a tablet secured sufficiently so that it may not be jarred loose under substantially any combination of blows or impulses, or even upon explosion of the balloon piece A. In one embodiment, once inserted, a fragrance tablet may be removed from the end cap of neck fitting 10 only by physical destruction of the tablet itself; for example by prying with a thin metallic implement such as a knife blade such that the tablet will not pop out but will result only in the partial destruction of the tablet, or such that the tablet flakes off into a harmless powder whenever contact is made with the prying element. Even with the removal of a portion of the tablet in this manner, the remainder is securely held in place until such remainder is reduced in size such that it is no longer engaged by a plurality of longitudinal rib 15.

The preferred design of the exterior portion of the lateral wall 11 of the neck fitting 10 is as shown in FIG. 1. The first part of the exterior of inner end 13 to engage balloon piece A includes a tapered portion 16 for ease of entry by centering with collar portion 30 and balloon piece A. This tapered portion 16 may conveniently be at an angle of 30 degrees from the exterior surface of lateral wall 11, but the angle could be adjusted within reasonable limits. The surfaces that are designed to come in contact with the balloon A, may be smoothly finished so as to avoid puncturing or snagging the balloon piece A. Continuing longitudinally downward toward end cap 12, it may be seen that the tapered portion 16 of the exterior of lateral wall 11 extends to a first cylindrical wall portion 17. The first cylindrical wall portion 17 serves to insure that the body of collar portion 30 is substantially centered about neck fitting 10 prior to engagement with first sealing member 18. The first sealing member 18 is inclined with respect to the first cylinder wall portion 17 to provide a seal or a partial seal upon engagement with collar portion 30 and balloon piece A; additionally, advantageously, due to the mating of neck fitting 10 and collar portion 30 with balloon A, the neck fitting 10 including the end cap 12 will not tend to separate from an applied impulse once insertion has been proceeded to the point at which even a partial seal has been made by engagement with tapered member 18. This surprising result will be described in more detail later.

Continuing longitudinally towards end cap 12, first sealing member 18 which is tapered is adjacent to a second cylindrical wall portion 19 which forms one of a plurality of seals when engaged with collar member 30 and balloon piece A. The lower extremity of said second cylindrical wall portion 19 is adjacent to and at substantially 90 degrees with a nearly transverse portion which serves as a locking member 21. Once the locking member 21 locks with the corresponding interlocking member of collar 30 which may be both at 90 degrees, it is virtually impossible to disconnect neck member 10 and collar member 30 without physically destroying one or the other. While this may be desired for some applications, it is deemed preferable for the majority of uses to implement the locking member 21 not with a right angle but with a slight greater angle such as 95 degrees. Such a construction will permit the neck fitting 10 to be disconnected from collar portion 30 by an adult without destruction of either the collar portion 30 or the neck fitting 10, but the difficulty required so to do is beyond the capability of small children and of children generally under the age of 12.

Additionally, locking member 21 serves as a second seal when engaged with the corresponding its interlocking member of collar portion 30. Locking member 21 connects to a third cylindrical wall member 22 which similarly provides a sealing function.

Projecting radically outward from cylindrical wall member 22 and end cap 12 in the preferred embodiment of FIG. 1 is a peripheral flange 23. The peripheral flange 23 provides a convenient grasping member when separating a connection unit and is also designed so as to provide a convenient support for attachment of a suction cup (not shown). The outer rim of said peripheral flange 23 is shown with a tapered portion 24 to permit a suction cup to be slipped easily over the peripheral flange 23. In this manner, an inflated balloon may be readily attached to any smooth surface, and the enjoyment therefore may be extended well beyond the normal time required for a lighter-than-air filled balloon to diffuse enough of its gases to cause it to be no longer lighter than air.

Turning now to the collar member 30 of FIG. 1, it may be seen that the exterior portion 31 of said collar member 30 is substantially cylindrical, the outermost corner 32 thereof being rounded or substantially at an angle of 90 degrees. As shown in FIG. 1 and FIG. 3, neck fitting 10 and collar portion 30 are formed as one-piece article.

FIG. 3 illustrates a portion of the collar ring portion 30 with a balloon A inserted through, and the mouth B of said balloon A is pulled over and encircling said collar ring portion 30.

In use, the mouth B of the balloon piece A will be inserted into the collar portion 30 first from the lower end 33 of the collar portion 30, as shown in FIG. 1; and the balloon piece A pulled through the interior portion 34 and the annulus 35, around the exterior portion 31; and placed snugly on the end piece 36. When in place, and prior to being inflated, the balloon piece A will be disposed about the collar member 30 substantially as shown in FIG. 3. To seal the balloon subsequent to inflation, it may be pinched off below the collar portion 30 and the neck fitting 10 may be inserted into collar portion 30, the connecting member 40 being flexible enough to permit this operation to be performed quite readily. As is apparent from FIG. 4, the upper end 37 of the collar portion 30, as oriented in FIG. 1 that first engages the neck fitting 10. To facilitate this initial engagement, the interior portion 38 of end piece 37 is tapered or beveled, preferably at an angle compatible with that of tapered portion 16 of neck member 10. The innermost annulus 35 will form a partial seal when engaged with the smaller diameter portion of the tapered surface 18, and a complete seal when the inner most annulus 35 engages the with third cylindrical wall portion 22 when completely engaged or "snapped" into place. Also, the transverse portion 39 similarly seals with corresponding locking member 21 of neck fitting 10 when fully engaged; should surface of the locking member 21 be formed at an angle greater than 90 degrees, then the surface of the transverse portion 39 may be formed at the right angle. Conversely, disassembly may also be permitted by forming the surface of the locking member 21 at the right angle and the surface of the transverse portion 39 at the slightly greater angle.

FIG. 2 shows the plug valve neck fitting 10 completely assembled with a typical valve—basket—insert 55 is shown in the top view of the plug valve neck fitting 10 and shows the connecting member 40 preferable may be formed to be flexible and in a strap-like configuration to connect the neck fitting 10 and the collar portion 30. The end portion 41 of the connecting member 40 which connects to the collar portion 30 is flared into a hand-like shape and includes three "fingers" 42, 43, and 44. Only the middle finger 43 is connected to the collar portion 30 in this embodiment. The balloon mouth B is consequently prevented by connecting member 40 from completely encircling end piece 35 at the junction thereof with connecting member 40 and the collar portion 30, the mouth B must necessarily be positioned below connecting member 40. Any tendency of said balloon piece A or mouth B to retract and thus slide off of collar portion 30 may be prevented by outer fingers 42 and 44. The balloon mouth B may be worked through the spaces between the outer fingers 42 and 44 so as to rest on the side of these fingers opposite to that of the balloon mouth and finger 43. In this configuration, the outer fingers 42 and 44, preferably being constructed of a resilient material, will then urge the balloon mouth B "upward" or outward toward end piece 36, thereby preventing the balloon from disengaging from collar portion 30. Connecting member 40 thus serves four functions: providing an apparatus for connecting the neck fitting 10 and the collar portion 30 during the manufacturing; providing a apparatus for tying a ribbon or string to it for holding balloon or hanging balloon aloft; distributing, and assembly operations; increasing safety of an assembled, inflated unit with respect to smaller children; and providing an apparatus to keep the balloon mouth engaged with the collar portion 30.

A number of safety features of the present invention have been mentioned, but the one of the advantageous features is undoubtedly the natural tendency of an assembled embodiment to increase the seal between neck fitting 10 and collar portion 30 when a balloon piece is subjected to sudden increases in pressure. It is well known that the pressure in the gas confined in a container is equal at all points, and that a sudden increase in pressure is transmitted almost instantly throughout the confined volume. It is also apparent that the end cap 12 of neck fitting 10 is exposed to the gas pressure of the balloon piece, and it was therefore to be expected that an increase in pressure would tend to force the end cap out from collar portion 30 and balloon piece A, perhaps even to cause the end cap 12 to be popped free from collar member 30. Such is not the case, however; it has been found by the inventor the inertial forces of gasket seal at work and may be readily demonstrated that the natural tendency of the assembly to move when subjected to increased pressure is in the direction of closure, not in the direction of separation. Further, it has been found that this natural tendency is not the result of the surfaces of the locking member 21 and traverse portion 39, but is substantially independent of any mechanical interlocking thereof. This latter statement is more easily demonstrable by only partially closing the assembly with an inflated balloon and then subjecting the balloon piece to an increase in pressure, i.e. by inserting neck fitting 10 into collar portion 30 only until the tapered portion of the first sealing member 18 of neck fitting 10 is engaged by the innermost annulus 35 of collar portion 30. At this point, neck fitting 10 is attached to the assembly only by connecting member 40 and a slight frictional engagement between tapered portion of the first sealing member 18, balloon piece A, and surfaces of the annulus 35 and of the second interior portion 38 of collar portion 30. The action of connecting member 40, to the extent it exerts any influence at all on the assembly, is that of an outward force on the collar portion 30 as its tendency is to return to its original, unfolded position; thus it is clear that the connecting member 40 makes little or no contribution of forces tending to further close the assembly, and if it contributes any forces at all, it is in the opposite direction, that of opening. Thus for all practical purposes, the engagement of neck fitting 10 with collar portion 30 at this point is frictional only, and with an inclined plane, tapered surface of the first sealing member 18, whose incline is such that any compressive force exerted by collar portion 30 would be expected to result in a force in the direction of opening rather than in the direction of closing. In fact, the neck fitting 10 is so loosely held at this point that it may be easily removed by hand. Surprisingly, then, an increase in pressure does not tend to pop out neck fitting 10 but tends to move the collar portion 30 further up the tapered surface of the first sealing member 18 in the direction of complete closure. In fact, should it be so desired, the inclination of tapered surface of the first sealing member 18 may be reduced somewhat from that of the preferred embodiment so that the motion upon reasonable increase in pressure will be sufficient to cause the neck fitting 10 and the collar portion 30 to completely engage, i.e., for the assembly to be self-sealing in the event of incomplete closure and subsequent increased pressure. In one embodiment, a greater inclination is employed such that complete closure will be affected only intentionally and will be indicated positively with an audible "snap". In any event, it is plain that the self-sealing tendency of the present invention is an advantageous safety feature for a device which is intended to be enjoyed by small children, even though the cause thereof may be imperfectly understood.

It is to be understood that the valve assembly of the present invention is gas-tight, or as practically so as may be realized in the real world and that inventor does not necessarily rely upon any leakage around such a valve assembly to emit the desired fragrances. Rather, it has been found that the fragrance from the interior of a balloon may be distributed at a satisfactory rate by diffusion through the balloon membrane itself. The present invention, by providing a "childproof" safety valve and assembly for retention of a fragrance tablet and other accessories avoids the safety hazard which would be present by a fragrance tablet and other accessories interior to but not secured within a balloon. Although the present invention has been described in terms of a balloon, the present invention is equally applicable to any inflatable device.

Alternatively, to just scented balloons it has been found by the inventor that a fragrance-carrying balloon may be created by injecting a fragrance-carrying powder or liquid into a balloon being used in accordance with the teachings of the present invention, or that such a balloon my be created by replacing the normal powder used in the manufacture of balloons with a fragrance-carrying powder. In either event, there is formed a balloon with fragrance formed in to the interior thereto which is not emitted at a rapid or controlled rate until subsequent inflation of a balloon. Still another alternative is the spraying, dipping, or injection of a liquid-carrying fragrance, but this has been found to be even less satisfactory than the other alternatives heretofore described.

Turning now to FIG. 4, FIG. 4 illustrates the scented tablet 50 and a valve—basket—insert 55 holding the object 51 such as a LED light device and the balloon A. The collar portion 30 and balloon A are shown not in actual engagement with said plug valve neck 10 fitting but spaced apart transversely there from for purposes of clarity. FIG. 4 provides the means of safely encapsulate not only a fragrance but other objects 51 such as a light and/or tone—carrying medium.

Figure 5A:
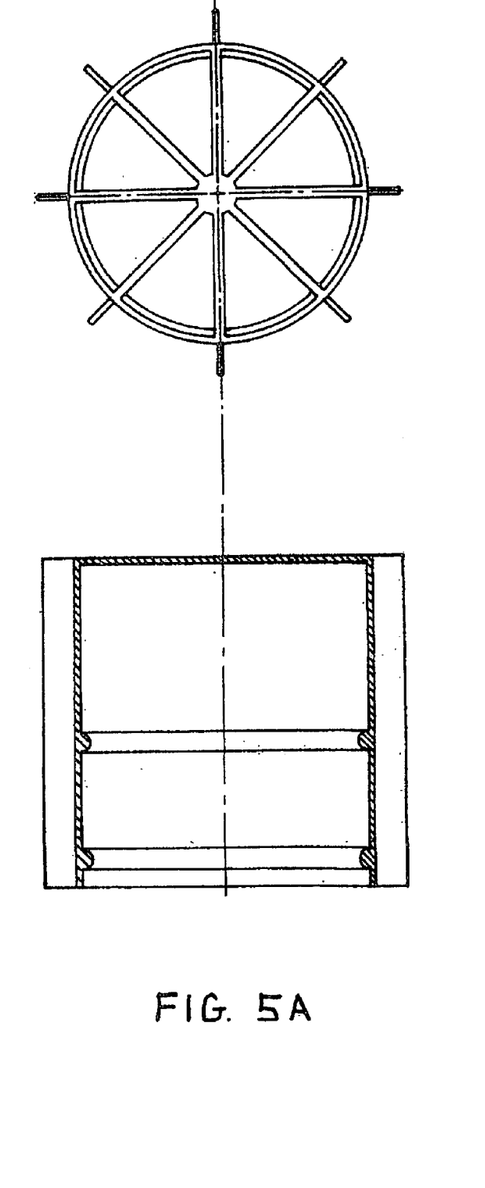
Figure 6A:
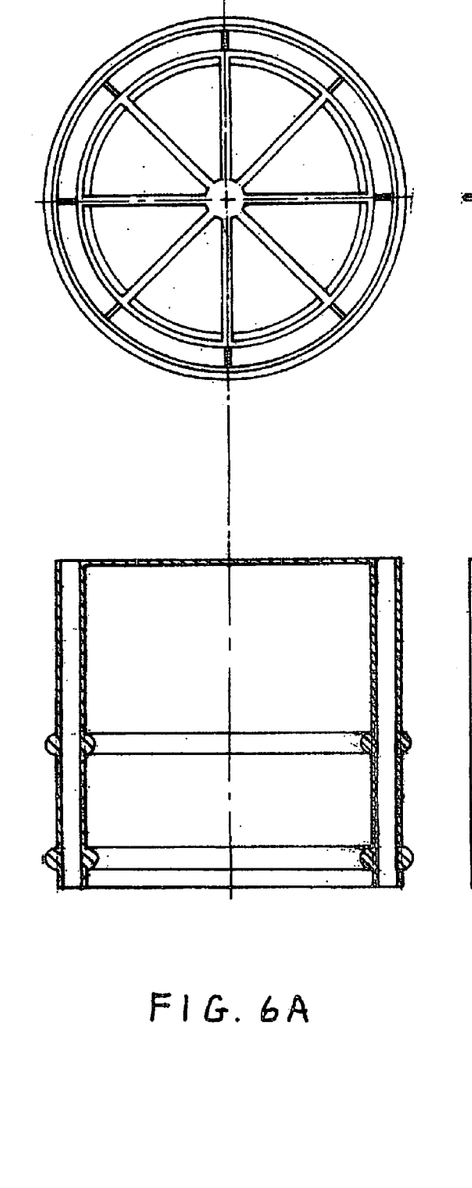

FIG. 5 is a side view of a valve—basket—insert 55. Substantially the right half of the insert 55 is shown in section whereas insert 55 section refers to also include the web 55 retainer of accessories and web 55 being attached to the receiving basket of 54 of object 51 (not shown) that are secured by O-rings 57 & 59 engagement encased in the inner basket 54. Attached to the outer portion of the inner basket 54 is spacing ribs 52 that connected to the inner basket 53 of which has O-rings 56 & 58 secured to matching O-ring of inner valve plug neck 10, a plan view or top view of this basket 53 is shown in FIGS. 6 and 6A. Additionally another valve—basket—insert 55 (shown in FIG. 5A) only excludes the basket 53 with O-rings 56 & 58 and subsequently the spacing ribs 52 are increased to have a friction fit with the valve plug neck 10.

Figure 7:
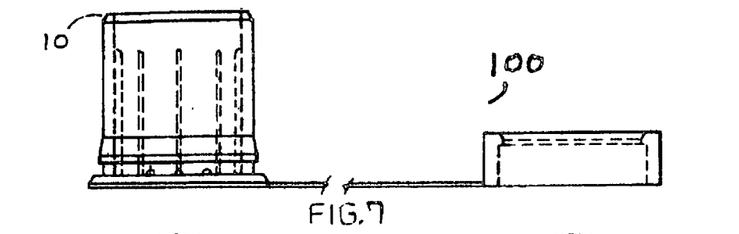
FIG. 7 is a side view of another preferred embodiment of the present invention with extended ribs for added tablets.

FIG. 7 shows another preferred embodiment of the present invention similar to that viewed in FIG. 1 and shown with the deletion of female O-rings 56 & 58 channeled in the interior plug valve neck fitting 10 as shown in FIG. 1. Additionally, FIG. 7 extends the internal ribs 15 to receive additional scented tablets 50 as viewed in FIG. 4.

Figure 8:
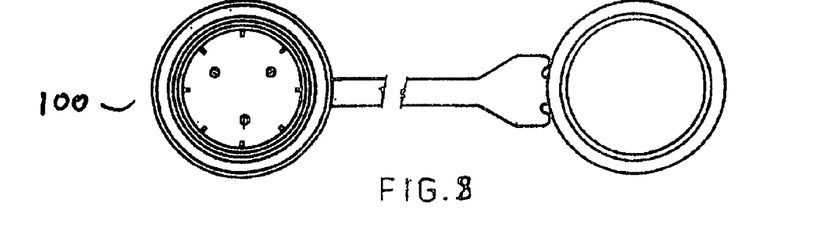
FIG. 8 is a top view of the embodiment shown in FIG. 7 showing ribs and raised platforms in orientation.

FIG. 8 shows the embodiment shown in FIG. 7 and shows the ribs 15 and raised platforms 14 (noted in FIG. 4) in orientation.

Figure 9:
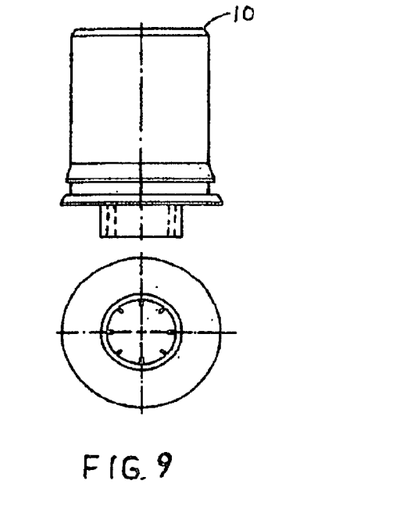
FIG. 9 is a side view and bottom view of another preferred embodiment showing a receiving cup with the ribs on the bottom of a typical plug valve and end cap.

FIG. 9 is another preferred embodiment showing a receiving cup with ribs 15 on the bottom of a typical plug valve 10 and end cap 12. The "receiving cup" may carry an object including but not limited to, a mini digital recorder, a straw or stick, a gondola, a radio control gondola with fan receiver/propulsion system and hand held transmitter/controller, a suction cup, etc.

Figure 10:
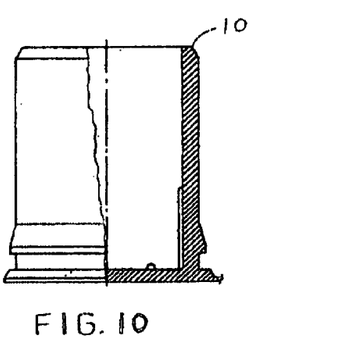
FIG. 10 is a side view of another preferred embodiment showing the right half of a plug valve neck as viewed in FIG. 7 but with short ribs.

FIG. 10 is another preferred embodiment showing the right half of a plug valve neck 10 as viewed in FIG. 7 but with short ribs 15.

Figure 11:
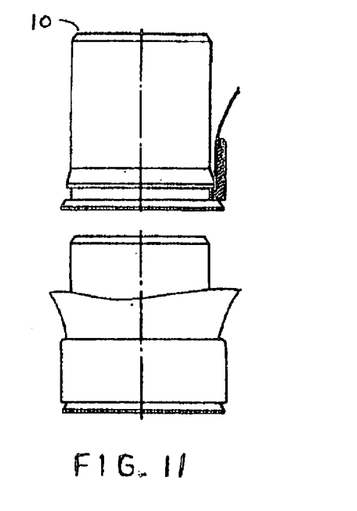
FIG. 11 is two side views of the collar ring engaged with the plug valve neck and balloon portion.

FIG. 11 shows the collar ring portion 30 engaged with the plug valve neck 10 in section of one view and completely assembled with balloon A sectioned off.

Figure 12:
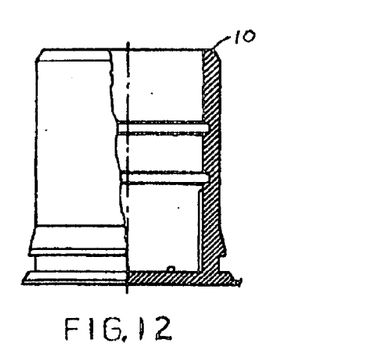
FIG. 12 illustrates a side view of the plug valve neck fitting of the present invention as shown in section of FIG. 1.

FIG. 12 illustrates a side view of the plug valve neck fitting of the present invention as shown in section of FIG. 1.

Figure 13:
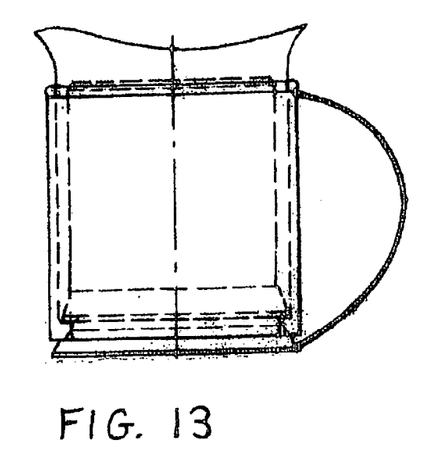
FIG. 13 is a side view of another preferred assembly with valve plug and extended collar to top of valve plug in closed position with balloon attached.

FIG. 13 is a side view of another preferred assembly with valve plug and extended collar 31 to top of valve plug 10 in closed position with balloon attached.

Figure 14:
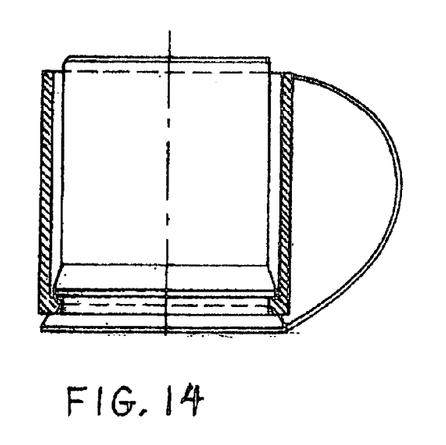
FIG. 14 is same side view of FIG. 13 except for collar in section without balloon.

FIG. 14 is same side view of FIG. 13 except for extended collar 31 shown in section without balloon A.

Figure 15:
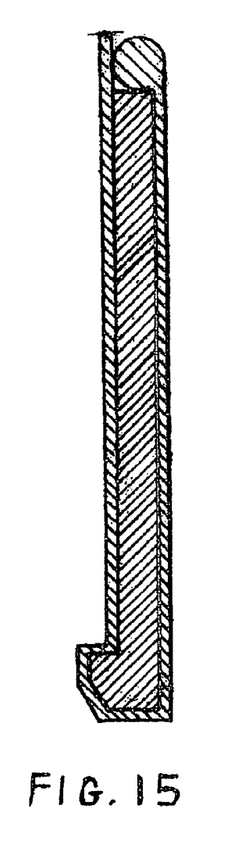
FIG. 15 is extended collar portion in section with balloon assembly.

FIG. 15 is extended collar 31 in section with balloon A neck attached and balloon body sectioned off.

Figure 16:
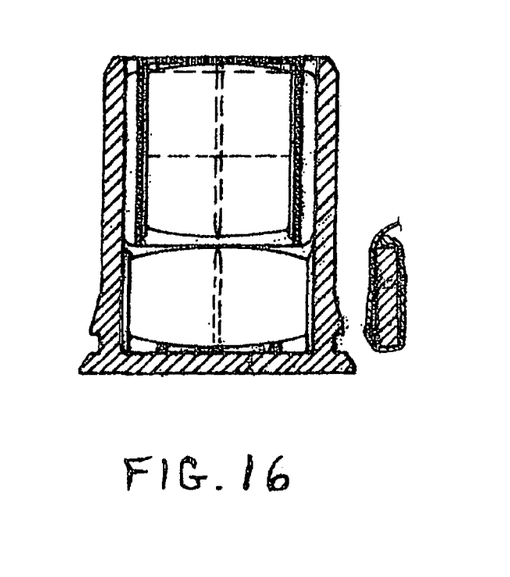
FIG. 16 is another preferred assembly shown in section with tablet, basket and collar.

FIG. 16 is another preferred assembly shown in section with tablet(s) 50, basket 55 holding object 51 such as a LED light device and/or tone-carrying medium . . . also, noted in this assembly is friction fitting ribs 52 holding tablet 50, basket 55 in plug valve and object(s) 51 in basket 55.

Figure 17:
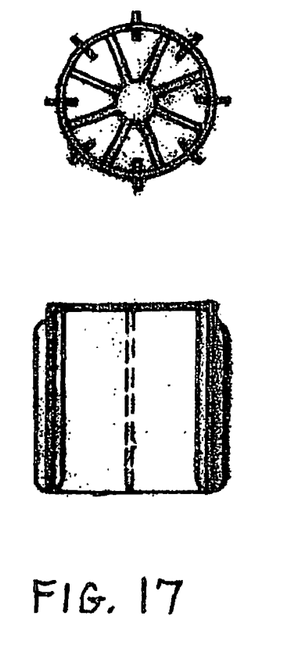
FIG. 17 is a side view in section and top view of another preferred basket as shown in FIG. 16.

FIG. 17 is a side view in section and top view of basket 55 as shown in FIG. 16.

Figure 18:
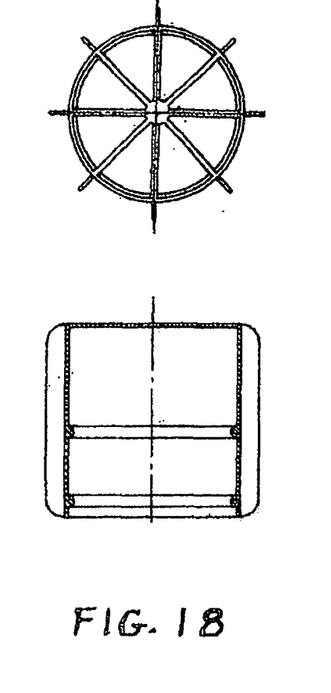
FIG. 18 is a side view in section and top view of another preferred basket to secure accessories with friction fit in valve plug.

FIG. 18 is a side view in section and top view of another preferred basket 55 to secure accessories . . . also, noted in t his assembly is friction fitting ribs 52 to hold basket 55 in plug valve and O-rings 57 & 59 in the inner basket 54 to secure object(s) 51.

Turning back to FIG. 4 and FIG. 9, with one of the means to safely encapsulated or carry not only a fragrance but other objects in the basket 55 and/or bottom receiving cup. Whereas, a mere balloon is now complete to affect the five senses, by compacting all within or on a safe valve assembly. Commercial devices are readily available to satisfy and meet the specifications of this invention and easily adapted to make a world of sense.

Although certain specific embodiments of the invention have been described herein in detail, the invention is not to be limited to only such embodiments, but rather by the appended claims.

The invention claimed is:

1. A massager balloon valve assembly, comprising:
   a holistic advertising balloon having a neck and a balloon body connected to the neck;
   a scent tablet to release a scent medium;

a neck fitting configured to inwardly extend substantially beyond the scent tablet of the scent medium to accommodate secured objects into the balloon body of the balloon;

a collar portion to accept said balloon and said neck fitting;

a basket positioned over the scent tablet and;

an O ring positioned on an outer surface of the basket and an inner surface of the neck insert to form an interference fit between the basket and the neck insert;

wherein the balloon valve assembly is configured to respond to a change of pressure from said balloon to urge said balloon and said collar portion together.

2. A balloon valve assembly as in claim 1, wherein said neck fitting includes a basket and/or cup to hold an object.

3. A balloon valve as in claim 1, wherein said neck fitting includes an apparatus to hold a pellet of scent medium.

4. A balloon valve as in claim 3, wherein said neck fitting includes a first support member positioned radially.

5. A balloon valve assembly as in claim 4, wherein said neck fitting includes a second support member positioned radially within an inner ring.

6. A balloon valve assembly as in claim 2, wherein said object includes a light emitting diode.

7. A balloon valve assembly as in claim 2, wherein said object includes a mini recorder.

8. A balloon valve assembly as in claim 2, wherein said object includes a handheld transmitter.

9. A balloon valve assembly as in claim 2, wherein said object includes a light medium device.

10. A balloon valve assembly as in claim 2, wherein said object includes a tone medium device.

11. A balloon valve assembly as in claim 2, wherein said object includes a gondola.

12. A balloon valve assembly as in claim 2, wherein said object includes a radio controlled gondola with a fan to move said balloon substantially horizontally.

13. A balloon valve assembly as in claim 2, wherein said object includes a straw.

14. A balloon valve assembly as in claim 2, wherein said object includes a stick.

15. A balloon valve assembly as in claim 2, wherein said object includes a suction cup.

16. A balloon valve assembly as in claim 2, wherein said object includes a heat source device.

17. A balloon valve assembly as in claim 2, wherein said object includes a modified plug valve flange with a one way check valve fill tube.

18. A balloon valve assembly as in claim 2, wherein said object includes a bitter tasting but harmless pure vegetable product on an exterior flange.

19. A balloon valve assembly as in claim 1, wherein the balloon valve assembly is used in conjunction with a scented, lighted and audio communication balloon.

20. A balloon valve assembly as in claim 1, wherein the balloon valve assembly is used in conjunction with a scented balloon.

21. A balloon valve assembly as in claim 1, wherein the balloon valve assembly is used in conjunction with a lighted balloon.

22. A balloon valve assembly as in claim 1, wherein the balloon valve assembly is used in conjunction with a audio communication balloon.

23. A balloon valve assembly as in claim 1, wherein the balloon valve assembly is used in conjunction with a scented and lighted balloon.

24. A balloon valve assembly as in claim 1, wherein the balloon valve assembly is used in conjunction with a scented and audio communication balloon.

25. A balloon valve assembly as in claim 1, wherein the balloon valve assembly is used in conjunction with a lighted and audio communication balloon.

* * * * *